US012617984B2

(12) United States Patent
Lindner et al.

(10) Patent No.: US 12,617,984 B2
(45) Date of Patent: May 5, 2026

(54) HYDROPHILIC HOTMELT ADHESIVE

(71) Applicant: The Procter & Gamble Company, Cincinnati, OH (US)

(72) Inventors: Torsten Lindner, Kronberg (DE); Gültekin Erdem, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 482 days.

(21) Appl. No.: 17/724,642

(22) Filed: Apr. 20, 2022

(65) Prior Publication Data

US 2023/0340305 A1 Oct. 26, 2023

(30) Foreign Application Priority Data

Apr. 20, 2021 (WO) ................ PCT/CN2021/088387

(51) Int. Cl.

| | |
|---|---|
| ***C09J 123/14*** | (2006.01) |
| ***A61F 13/539*** | (2006.01) |
| ***A61L 15/24*** | (2006.01) |
| ***A61L 15/58*** | (2006.01) |
| ***C09J 7/35*** | (2018.01) |

(52) U.S. Cl.

CPC ........... *C09J 123/14* (2013.01); *A61F 13/539* (2013.01); *A61L 15/24* (2013.01); *A61L 15/58* (2013.01); *C09J 7/35* (2018.01); *A61F 2013/5395* (2013.01); *C09J 2423/10* (2013.01)

(58) Field of Classification Search

CPC ........ C09J 123/14; C09J 7/35; C09J 2423/10; A61F 13/539; A61F 2013/5395; A61L 15/24; A61L 15/58

See application file for complete search history.

(56) References Cited

U.S. PATENT DOCUMENTS 5,885,266 A 3/1999 Chihani et al.
6,146,757 A * 11/2000 Mor .......................... D01F 6/06 428/364
6,380,292 B1 4/2002 Gibes et al.
6,632,206 B1 * 10/2003 Onishi .................. A61F 13/495 604/385.01
9,238,763 B2 1/2016 Tripathy et al.
11,306,226 B2 4/2022 Hu et al.
2004/0081795 A1 4/2004 Wang et al.
2005/0288412 A1 * 12/2005 Hohner .................. C09J 123/10 524/487

(Continued)

FOREIGN PATENT DOCUMENTS

EP 0710737 A2 5/1996
WO 9748779 A1 12/1997

(Continued)

OTHER PUBLICATIONS

All Office Actions; U.S. Appl. No. 17/684,457, filed Mar. 2, 2022.

(Continued)

*Primary Examiner* — Jeremy R Pierce
(74) *Attorney, Agent, or Firm* — Anna E. Haller; Amanda Herman Berghauer; Daniel S. Albrecht

(57) ABSTRACT

A hotmelt adhesive comprising a metallocene-catalyzed polyolefin and a hydrophilic melt additive. The adhesive is permanently hydrophilic and can be in particular used to bond components of a disposable hygienic article such as a diaper.

19 Claims, 2 Drawing Sheets

(56) References Cited

U.S. PATENT DOCUMENTS

| | | | | |
|---|---|---|---|---|
| 2013/0225752 | A1* | 8/2013 | Tse | C09J 123/10 524/505 |
| 2014/0324006 | A1* | 10/2014 | Zhong | A61L 15/225 524/505 |
| 2014/0358100 | A1 | 12/2014 | Remmers | |
| 2015/0299526 | A1* | 10/2015 | Gray | C08K 5/0016 524/153 |
| 2016/0102230 | A1* | 4/2016 | Gray | C09J 123/142 524/141 |
| 2018/0162971 | A1* | 6/2018 | Chen | C08F 110/06 |
| 2018/0256773 | A1* | 9/2018 | Lindner | A61L 15/24 |
| 2019/0144719 | A1 | 5/2019 | Wang et al. | |
| 2020/0157385 | A1 | 5/2020 | Kauffman et al. | |
| 2022/0332985 | A1 | 10/2022 | Lindner et al. | |

FOREIGN PATENT DOCUMENTS

| | | | |
|---|---|---|---|
| WO | 200000229 | A1 | 1/2000 |
| WO | 2014194074 | A1 | 12/2014 |
| WO | 2018027055 | A1 | 2/2018 |

OTHER PUBLICATIONS

PCT Search Report and Written Opinion for PCT/CN2021/088387 dated Oct. 1, 2021, 13 pages.

* cited by examiner

HYDROPHILIC HOTMELT ADHESIVE

CROSS REFERENCE TO RELATED APPLICATION

This application claims the benefit, under 35 U.S.C. § 119(b), of PCT Patent Application Serial No. PCT/CN2021/088387, filed on Apr. 20, 2021, the entire disclosure of which is incorporated herein by reference.

FIELD OF THE INVENTION

The invention relates to hotmelt adhesives having hydrophilic properties. The hydrophilic hotmelt adhesives of the invention can be used in personal hygiene absorbent articles, such as diapers or feminine protections. The hydrophilic hotmelt adhesives facilitate the transfer of a fluid such a urine transfer from one layer of the article to another layer. The hydrophilic hotmelt adhesives may be used to bond a nonwoven to another layer, such as a second nonwoven or an absorbent material.

BACKGROUND OF THE INVENTION

Nonwovens are used as topsheet, acquisition layer or core wrap in disposable articles such as diapers, adult incontinence products and sanitary napkins. In these articles, it is necessary to adhere the nonwoven to another layer of the article. This second layer may be another nonwoven, a tissue, or an unrelated material such as an absorbent material. A commonly employed technique to bond the components of the absorbent article is the use of a hotmelt adhesive. Hotmelt adhesives allow for cost and time efficient manufacturing, since there is no evaporation step necessary as is the case for water based or solvent based adhesive systems. Suitable hotmelt adhesives must possess excellent adhesion to the substrates involved. For nonwoven applications they must also possess good flexibility, no staining or bleed through, suitable viscosity, set speed and open time to function on commercially available equipment, and acceptable thermal aging properties.

In personal hygiene article such as disposable diapers, sanitary napkins and bed pad constructions, it is desired to draw the moisture away from the body and into the absorbent core as quickly as possible after the article is wetted. Nonwovens which have been hydrophillically treated have been proposed. WO 2017/156234 A1 (P&G, Lindner et al.) discloses material webs comprise a hydrophobic or hydrophilic melt additive that can be activated in localized areas by thermal energy. WO 2018/165511 A1 (P&G, Lindner et al.) discloses a permeable nonwoven comprising fibers and/or filaments made of a polymer matrix comprising a hydrophilic melt additive and/or a tactile modifying melt additive. Spunbond PP nonwoven comprising hydrophilic melt additives are for examples disclosed in U.S. Pat. No. 6,146,757 (Techmer).

It has also been proposed to use hotmelt adhesives having the ability to facilitate the transmission of an insulting liquid from a nonwoven layer towards the absorbent material, in order to achieve quicker fluid transmission. WO 00/00229 (P&G, Lindner et al.) discloses hygienic articles comprising an oil resistant, hydrophilic adhesive. The formula of the adhesive or its permanency is however not disclosed. U.S. Pat. No. 6,380,292 B1 (Bostik) discloses hydrophilic hotmelt adhesive compositions suitable for nonwoven disposable articles which are prepared by blending various adhesive components with a surfactant, including high amount of tackifiers. Commercially available tackified hotmelt adhesives are typically found to be not permanently hydrophilic, i.e. they lose their hydrophilicity over time or under conditions of accelerated aging.

There is a need for hydrophilic hotmelt adhesive compositions that are safe for use in personal absorbent articles, retain their hydrophilic properties over time and are cost-effective.

SUMMARY OF THE INVENTION

In a first aspect, the invention is directed to a hydrophilic hotmelt adhesive comprising a metallocene-catalyzed polyolefin and a hydrophilic melt additive. The metallocene-catalyzed polyolefin may be in particular a propylene-ethylene copolymer. The metallocene-catalyzed polyolefins may in particular have a peak molecular weight ranging from 10,000 g/mol to 130,000 g/mol, wherein the peak molecular weight is measured according to the Peak Molecular Weight (Mp) Measurement Method disclosed herein. Suitable hydrophilic melt additives are amphiphilic molecules, comprising a hydrophilic group and a hydrophobic group. Preferred, non-limiting, commercial examples of propylene-ethylene copolymers and hydrophilic melt additives are described further below in the description. The invention provides hotmelt adhesives that can exhibit a Fresh Film Contact Angle and an Aged Film Contact Angle with distilled water of less than 70 degrees, preferably of less than 50 degrees, as measured by the Contact Angle Test described herein.

In a second aspect, the invention is directed to a personal hygiene absorbent article, such as a diaper or an adult incontinence product, comprising the hydrophilic hotmelt adhesive of the invention. The hotmelt adhesive can be in particular used to directly bond a pair of layers selected from (not exhaustive list):

- the topsheet and the acquisition layer; and/or
- the top and bottom layers of a three-dimensional laminate (e.g., topsheet); and/or
- the acquisition layer and the absorbent core; and/or
- the topsheet and the absorbent core, if these are in direct contact;
- the core wrap and the absorbent material.

Without wishing to be bound by theory, the inventors believe that the working principle of a hydrophilic melt additive can be transferred from PP fibers used in nonwovens to propylene rich polymer blends used as hotmelt adhesives. In this model, the engineered incompatibility of the melt additive and host polymer at lower temperature provides a thermodynamic driving force for blooming and an enrichment in the melt additive molecules at the surface of the host metallocene-catalyzed polyolefin polymer. The melt additive is further anchored at the surface of the host polymer via its hydrophobic group. This prevents the hydrophilic additive molecules from migrating out of the adhesive onto other layers of the absorbent articles (e.g., transferring to barrier layer nonwovens, hence making them permeable to liquid), while maintaining the hydrophilicity of the hotmelt adhesive. The hotmelt adhesives of the invention are also compatible with typical skincare lotions that may be present on the topsheet or used by a caregiver.

This and other aspects of the invention are described herein and in the appended claims.

DETAILED DESCRIPTION OF THE INVENTION

Preamble

Figure 1:
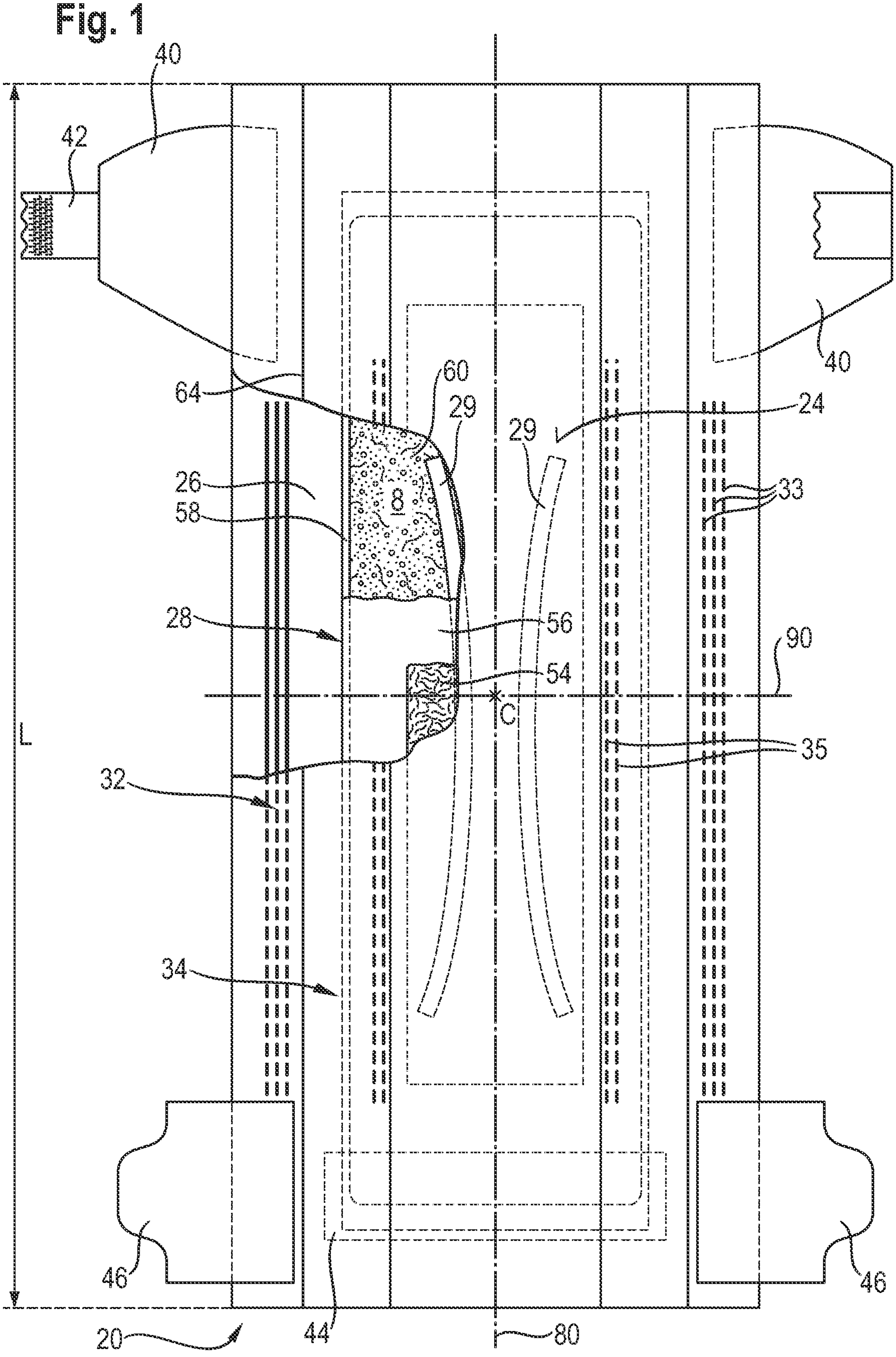
FIG. 1 is a schematic view of an exemplary taped diaper that may employ the adhesive of the invention.

"Comprise", "comprising", and "comprises", as used herein, are open ended terms, each specifies the presence of what follows, e.g., a component, but does not preclude the presence of other features, e.g., elements, steps, components known in the art, or disclosed herein. Any features indicated below is optional unless indicated otherwise. Unless otherwise specified, each of the components of the invention may comprise one or more sub-components having the specified properties. For example, "a metallocene-catalyzed polyolefin" means "one or more metallocene-catalyzed polyolefin(s)" having the specified properties, for example molecular weight. All % are by weight of the adhesive composition unless indicated otherwise.

Hotmelt Adhesives

Conventional hotmelt adhesives are hydrophobic in nature and form a barrier to the transfer of fluid between layers, in particular between the topsheet and the absorbent core, hindering aqueous materials, e.g., moisture, water, blood, urine, menses, to flow into the core. The hydrophilic hotmelt adhesives of the invention on the other hand facilitate the transmission of an aqueous material such as urine from the topsheet to the absorbent core, due to its low contact angle.

In its simplest form, the hotmelt adhesives of the invention comprise a metallocene-catalyzed polyolefin and a hydrophilic melt additive. These and additional optional components are described in further details below.

Metallocene-Catalyzed Polyolefin(s)

The hydrophilic hotmelt adhesive of the invention comprises a ("one or more") metallocene-catalyzed polyolefin. The metallocene-catalyzed polyolefin is typically the main component by weight of the hotmelt adhesive. The hotmelt composition may typically comprise at least 30% by weight of the metallocene-catalyzed polyolefin (or mixture thereof), in particular at least 40%, or at least 50%, or at least 60%, or at least 70%, by weight.

The invention may use a blend of two or more metallocene-catalyzed polyolefins. However, the invention may be carried out with one metallocene-catalyzed polyolefin, which simplifies production. A commercial example of metallocene-catalyzed polyolefin that may be formulated as single polyolefin in the hotmelt adhesive is Licocene® PP 2502, from Clariant. In its simplest form, the hydrophilic hotmelt adhesive consists substantially of one such polyolefin and a hydrophilic melt additive.

While the invention is not limited to a particular type of metallocene-catalyzed polyolefins, propylene-based metallocene-catalyzed polyolefins are preferred. The propylene-based metallocene-catalyzed polyolefins may be homopolymers or copolymers. Propylene-based co-polymers may comprise at least 50% of propylene monomers by weight of the copolymer. Co-polymers are preferably propylene-ethylene copolymers. Propylene-ethylene copolymers comprise at least 50% by weight of the copolymer of propylene monomers, in particular at least 60%, or at least 70%, or at least 80% by weight. The remaining monomers are ethylene monomers, and optionally other alpha olefin monomers may be present in the co-polymers, for example 4-methyl-1-pentene, pentene-1, 2-methylpentene-1, 3-methylbutene-1, heptene-1, dimethylpentene-1, trimethylbutene-1, ethylpentene-1, methylpentene-1, trimethylpentene-1, methylethylpentene-1, 1-octene, diethylbutene-1, propylpentane-1, decene-1, methylnonene-1, nonene-1, trimethylheptene-1, methylethylbutene-1, dodecene-1, and hexadodecene-1, and combinations thereof. The exact monomer distribution is typically published by the supplier, but can also be determined by a suitable method, such as nuclear magnetic resonance or infrared spectroscopies.

Suitable metallocene-catalyzed propylene-ethylene copolymers are commercially available from Clariant under the polymer range Licocene®, with a broad range of properties such as molecular weight, viscosity, crystallinity, etc. . . . US 2016/053,149A1 assigned to Clariant also describes suitable co-polymers. These examples were produced by the processes indicated in EP 571,882. For a given catalyst system and given comonomer ratio, the molecular weight was regulated via the hydrogen partial pressure as molar mass regulator. Other suitable commercially available metallocene-catalyzed propylene-ethylene copolymers are available as Vistamaxx® copolymers from Exxon. Vistamaxx typically have a higher molecular weight than Licocene copolymers. Metallocene-catalyzed propylene homopolymers are available from Idemitsu Kosan Co., Ltd under the tradename L-MODU™, in particular L-Modu S-410. L-Modu feature high thermal stability, are odorless, and not sticky by narrow molecular weight distribution.

Metallocene-catalyzed polyolefins suitable for the invention may have a peak molecular weight in the range of from 10,000 g/mol to 800,000 g/mol, wherein the peak molecular weight is measured according to the Peak Molecular Weight (Mp) Measurement Method disclosed herein. Advantageously, the hotmelt composition comprises a relatively low molecular weight metallocene-catalyzed polyolefin having a peak molecular weight below 130,000 g/mol. The peak molecular weight of the metallocene-catalyzed polyolefin may be for example in the range of from 10,000 g/mol to 130,000 g/mol, in particular from 20,000 g/mol to 70,000 g/mol.

Table 1 discloses the peak molecular weight (Mp) in g/mol of some commercially available polymers that may be used in the invention.

TABLE 1

| | Mp |
|---|---|
| Licocene PP 1302 | 24,100 |
| Licocene PP 1602 | 75,900 |
| Licocene PP 2502 | 57,100 |
| Licocene PP 3602 | 80,000 [1] |
| Vistamaxx 3000 | 299,500 |
| Vistamaxx 6102 | 687,700 [1] |
| Vistamaxx 6202 | 330,800 [1] |
| Vistamaxx 6502 | 185,300 |

[1]) correlated (not measured directly)

Metallocene-catalyzed polyolefins typically have a regular spatial repeat monomer unit distribution and a narrow molecular weight distribution, as is known in the art. Metallocene-catalyzed polyolefins useful in the present invention may be described as low- or semi-crystalline with an enthalpy of fusion, as measured according to the Enthalpy of Fusion Test Method described below, typically ranging of from 5 J/g to 45 J/g. Table 2 discloses the enthalpy of fusion in J/g of some commercially available polymers that may be used in the invention:

TABLE 2

| | Enthalpy of Fusion |
|---|---|
| Licocene PP 1302 | 11.8 |
| Licocene PP 1602 | 16.7 |
| Licocene PP 2502 | 29.4 |
| Licocene PP 3602 | 35.0 |

Hydrophilic Melt Additives

The hotmelt adhesives of the invention comprise a hydrophilic additive. As for the other components indicated, the hotmelt adhesive composition may comprise one, two or more, of such hydrophilic additives. Hydrophilic melt additives are amphiphilic molecule having a hydrophilic head and a hydrophobic tail. The hydrophilic head is oriented towards the surface of the adhesive, thus providing for the hydrophilic character of the adhesive, while the hydrophobic head remains in the polymer matrix. The hotmelt adhesives of the invention have particularly stable hydrophilic properties, enabled by the compatibility of the metallocene-catalyzed polyolefin and the hydrophilic melt additive.

Hydrophilic melt additives are typically compounded in a masterbatch in the form of pellets than can be incorporated by homogenous mixing in the molten polyolefin. Commercial examples of hotmelt additives particularly compatible with a propylene-based metallocene-catalyzed polyolefin are PPM 15560 from Techmer (hydrophilic PP masterbatch) and Brij S2 (Croda). Further, in order of declining preference, Brij S10 (from Croda,) Unithox 450, Unithox 720 and Unithox 750 (from Baker Hughes) can be used. PPM 15560 is preferably used in a dosage of 0.5 weight percent of the masterbatch, Brij S2 and Brij S10 in a dosage of preferably 2 weight percent of the active. Techsurf® melt additives from Techmer have been used to impart hydrophilicity to polyolefin fibers, nonwoven fabrics, and specialty plastic applications, and are useful in the present invention.

U.S. Pat. No. 6,146,757 discloses a hydrophilic melt additive comprising a blend of a first wetting agent and a second wetting agent. The first wetting agent is at least one water insoluble nonionic alkoxylated alkyl phenol, and the second wetting agent is at least one compound selected from the group consisting of an alkoxylated fatty alcohol and a water-soluble, nonionic, nonhydrolyzable polyoxyalkylene-modified organosilicone polymer. While not wishing to be bound by theory, it is believed that Techmer PPM 15560 is a melt additive according to this formula, in particular wherein the first wetting agent is a an ethoxylated nonylphenol having about 4 moles of ethylene oxide and the second wetting agent is a water-soluble, nonionic, non-hydrolyzable polyoxyalkylene-modified organosilicone polymer. However, this example is not limiting the present invention, which can be reduced in practice with other melt additives, as exemplified above.

The additives of the Brij® series from Croda are ethoxylated alcohols of the general formula:

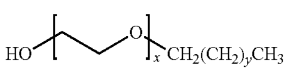

with x ranging from 2 to 100 and y ranging from 12 to 24, in particular y=16 (stearyl).

For example, Brij S2 with x=2 and y=16 has a low molecular weight of 386 g/mol, which presumably facilitates the diffusion to the surface. These ethoxylated alcohols may be a more cost-effective alternative to the above mentioned blend. The blends described in U.S. Pat. No. 6,146,757 were found to enable a stronger hydrophilic effect, while Brij S2 enables a milder hydrophilic effect. One or the other additive may be thus preferred depending on the application purpose. In some applications (such as bonding of the topsheet to the acquisition layer), a milder hydrophilicity may be preferred to facilitate the draining of the top layer by lower layers in the diaper, and avoid liquid remaining in the top layer being exposed to the consumer.

Optional Components

Optional components may be further added to the hydrophilic hotmelt adhesive, as is known in the art, in particular tackifier, plasticizer, antioxidant, and the like.

Tackifiers otherwise called "tackifier resins" or "tackifying resins" are low-molecular weight compounds (oligomers) that are added to adhesive formulations to improve tack and peel adhesion materials. Usual tackifiers known in the art may be used in the present invention. Typical tackifiers are thermoplastic materials stable at least up to 200° C., being amorphous glasses at room temperature, and having a Tg higher than 50° C., preferably comprised between 80° C. and 125° C. Tackifiers typically have a molecular weight comprised between 500 and 2000 Daltons.

Tackifiers are in general organic chemicals with polycyclic structure. Commonly used tackifiers are selected from rosin resins and their derivatives (rosin esters), hydrocarbon resins produced from petroleum-based by-products of naphtha crackers, and terpene resins (modified or not). Hydrocarbon resins may be aliphatic, cycloaliphatic and aromatic resins (in particular C5 aliphatic resins, C9 aromatic resins, and C5/C9 aliphatic/aromatic resins), and may be optionally hydrogenated hydrocarbon resins.

Exemplary tackifiers include aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpenes, aromatic modified poly-terpenes, terpene-phenolics, aromatic modified hydrogenated poly-cyclopentadiene resins, hydrogenated aliphatic resins, hydrogenated aliphatic aromatic resins, hydrogenated terpenes and modified terpenes, and hydrogenated rosin esters. Particularly suitable tackifiers are rosin (and its derivatives) resins and hydrogenated hydrocarbon tackifiers, which are solid at room temperature.

However, the hotmelt adhesive of the invention has the advantage that it may be relatively simply formulated with low amount of tackifiers (below 40% by weight, in particular below 20% or even 10% by weight), or even be free of tackifiers. There are several advantages to hotmelt adhesives with low amount or no tackifier. Firstly, as indicated, this reduce the complexity of the formulation and for example facilitate quality control and traceability of the ingredients. Second without these tackifiers, the hotmelt adhesive may be used for application where tackiness at room temperature is not desired, such as bonding a three dimensional topsheet to a flat substrate, in order to avoid bonding and thus flattening of the layers outside of the desired bonding areas.

Reducing or eliminating tackifiers from the adhesive composition also allows applying the hotmelt adhesive composition on a substrate, e.g., a nonwoven, as a hydrophilic coating outside a converting line, for example at a supplier. Because the coating is not tacky, the coated substrate can be conditioned and stored for later transport and usage, typically in the form of rolls of the coated substrate. For example, the hydrophilic hotmelt adhesive may be coated on a continuous acquisition layer material in any desired pattern, and this coated material then be formed into a roll for later use in a converting line for absorbent articles. Due to the properties of the hotmelt adhesive, the coating acts as a durable and non-migrating hydrophilic coating on the acquisition layer material (or any substrate) providing durable hydrophilicity benefit under the topsheet.

A plasticizer can be present in the composition of the present invention. The plasticizer may be typically present in amounts of up to about 20% by weight, preferably up to about 10 wt %, based on the total weight of the hotmelt adhesive. Plasticizer can provide desired viscosity control without substantially decreasing the adhesive strength, the service temperature of the adhesive, and hydrophilicity of the adhesive. Typical plasticizers include usual plasticizing oils, such as mineral oil, naphthenic, paraffinic, Gas to Liquid (GTL) oil, but also olefin oligomers and low molecular weight polymers, as well as vegetable and animal oil and derivatives of such oils, can be used. There are significant advantages to minimizing or avoiding the use of a mineral oil. This can reduce the cost of the hotmelt composition, as well as eliminate an additional ingredient and potential issues that may be associated with supplying the additional ingredient.

The hotmelt adhesive may optionally comprise an antioxidant. Non-limiting examples of suitable antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetrakis [(methylene(3,5-di-t-butyl-4-hydroxyhydrocinnamate)]methane (e.g., IRGANOX™ 1010, from Ciba Geigy, New York); octadecyl-3,5-di-t-butyl-4-hydroxycinnamate (e.g., IRGANOX™ 1076, commercially available from Ciba Geigy) and combinations thereof. When used, the amount of the antioxidant in the hotmelt composition can be respectively less than 1%, alternatively from about 0.05% to about 0.75%, and alternatively from about 0.1% to about 0.5%, by weight of the hotmelt adhesive.

The hotmelt adhesive may optionally comprise a UV stabilizer that may prevent or reduce the degradation of the composition by radiation. Any UV stabilizer known to a person of ordinary skill in the art may be used in the hotmelt composition. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds, and combinations thereof. Where used, the amount of the UV stabilizer in the hotmelt adhesive can be less than 1%, alternatively from about 0.05% to about 0.75%, and alternatively from about 0.1% to about 0.5%, by weight of the hotmelt composition.

The hotmelt adhesive may optionally comprise a brightener, colorant, and/or pigment. Any colorant or pigment known to a person of ordinary skill in the art may be used in the hotmelt composition. Non-limiting examples of suitable brighteners, colorants, and/or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant, and/or pigment in the hotmelt composition can be less than 10%, alternatively from about 0.01% to about 5%, and alternatively from about 0.1% to about 2%, by weight of the hotmelt composition.

The hotmelt composition may optionally comprise a fragrance such as a perfume or other odorant. Such fragrances may be retained by a liner or contained in release agents such as microcapsules that may, for example, release fragrance upon removal of a release liner from or compression on the adhesive composition. Where used, the amount of the fragrance in the hotmelt composition can be less than 3%, alternatively less than 2%, alternatively less than 1%, alternatively from about 0.05% to about 0.75%, and alternatively from about 0.1% to about 0.5%, by weight of the hotmelt composition.

A low contact angle is desirable so that water, urine or other water-based discharges "wet out" rather than "bead up" resulting in the fluid being directed into the absorbent core and away from the topsheet. The hydrophilicity of an adhesive can be quantified by the Contact Angle Method described hereinafter. In order to be particularly suitable for the absorbent article of the present invention, the hotmelt adhesives preferably have a contact angle with distilled water of less than 70°, more preferably less than 50° C., and retain this property after ageing (see Contact Angle Method described herein).

Compounding

The hotmelt adhesive can be prepared by heating the metallocene-catalyzed polyolefin(s) at sufficiently elevated temperatures (e.g., about 135° C. to about 175° C.) to melt the polymers. The melt additive and other ingredients are added to this molten primary polymer blend. A mixer can be used to mix the polymers and other additives together into a final hotmelt composition.

The resulting blend is cooled and conditioned for transport and storage. During application, the hotmelt composition is molten again and can be applied to a substrate using any known applicator devices, in particular spray which is a non-contact application.

Other Properties

The hotmelt adhesive according to the invention preferably has a viscosity at 170° C. is in the range from 100 mPa·s to 10,000 mPa·s, in particular from about 1,000 mPa·s to about 7,000 mPa·s, as measured according to the Viscosity Test Method as described herein.

The hotmelt adhesive may also advantageously have a storage modulus (G') that is higher than $0.3\times10^6$ Pa at 37° C., as measured with Oscillatory Rheometry Test Method described below. The relatively high G' value at 37° C. is indicative of an adhesive that is not tacky during use. The hot-melt adhesive may in particular have a storage modulus higher than $1.0\times10^7$ Pa at 37° C., or even $1.5\times10^7$ Pa at 37° C. On the other hand, the hotmelt adhesive may also have a storage modulus (G') that is lower than $2.0\times10^8$ Pa at 37° C.

The hotmelt adhesive may also have a storage modulus (G') higher than $0.3\times10^6$ at 23° C., or even $1.5\times10^7$ Pa at 23° C., or even $2.0\times10^7$ Pa at 23° C. On the other hand, the hotmelt adhesive may also have a storage modulus (G') that is lower than $3.0\times10^8$ Pa at 23° C. Typically the G' value of polymers decreases with the temperature.

Commercially available propylene-ethylene copolymers such as those from Clariant's Licocene® have the following G', as measured as indicated below: Licocene® PP 1502 has a G' value of $1.4\times10^7$ Pa at 23° C. and $1.0\times10^7$ at 37° C., Licocene® PP 1602 has a G' value of $1.2\times10^7$ at 23° C. and $8.6\times10^6$ at 37° C., Licocene® PP 2502 has a G' value of $5.2\times10^7$ at 23° C. and $3.3\times10^7$ at 37° C.

The hotmelt adhesive may preferably also have a storage modulus (G') higher than $0.3\times10^6$ at 60° C. (reflecting storage conditions in countries with hot climate, as e.g., measured in containers). The hotmelt adhesive may also have a storage modulus (G') higher than $0.3\times10^6$ at 70° C., as indicative of the temperature which the hotmelt has in the process (after initial cool-down due to heat exchange with the substrate onto which it has been applied) when it gets into contact with aperturing tooling.

Absorbent Article 20

The hydrophilic hotmelt adhesive of the invention may be used to form bonds in absorbent articles. "Absorbent articles", as used herein, refers to personal hygiene products that are placed against or in proximity to the body of the wearer to absorb and contain the various exudates discharged from the body. Absorbent articles include baby diapers, training pants, adult incontinence undergarments, feminine hygiene products, bed matt, changing matt and the like. In another form, the absorbent article may be an insert for use with a reusable outer cover. As used herein, the term "body fluids" or "body exudates" includes, but is not limited to, urine, blood, vaginal discharges and fecal matter. These articles are typically disposable, meaning are not intended to be laundered or otherwise restored or reused as a hygienic article after a single use. Disposable absorbent articles typically comprise a liquid pervious topsheet, a liquid impervious backsheet and an absorbent core positioned between the topsheet and the backsheet.

An exemplary taped diaper 20 is represented in FIG. 1. This diaper is shown for illustration purpose only as the present invention is applicable to a wide variety of diapers or other absorbent articles. The absorbent article 20 notionally comprises a longitudinally centerline 80 dividing the article in a left side and a right side, and a perpendicular transversal centerline 90 disposed at half the length of the article as measured on the longitudinal centerline 80, with both centerlines crossing at the center point C.

Typical diapers components include, from top to bottom, the topsheet 24, an acquisition layer (or system) 54, an absorbent core 28 and the backsheet 26. Inner and outer lateral barrier cuffs 34, 32, which are preferably elasticized with elastic strands 35, 33 respectively are typically present. The acquisition system may comprise a single layer (typically a hydrophilic air-through bonded carded nonwoven) or two or more layers as is known in the art. Elasticized back ears 40 having a tape end 42 can be attached to a landing zone 44 at the front of the article. Front ears 46 are typically present in such taped diapers to improve containment and attachment.

The absorbent core 28 can absorb and contain liquid received by the absorbent article and comprise a layer 8 of absorbent material 60, which may be a blend of superabsorbent polymer particles and cellulose fibers or pure superabsorbent polymer particles. The top side of the core wrap may be at least partially bonded by an adhesive according to the present invention, which thus at least partially immobilize the absorbent material within the core wrap. The absorbent core 28 may comprise absorbent material free channels 29, through which the top side 56 of the core wrap may be bonded to the bottom side 58 of the core wrap. The core wrap bonds may at least persist as the absorbent core 28 swells upon liquid absorption and creates three-dimensional channels at the wearer-facing surface of the article. Of course, this is entirely optional, the absorbent core may also not have bonded channels, or even unbonded channels. The absorbent material layer may be rectangular as show in in FIG. 1, but it is also common to have a shaped area which is tapered in the area around the transverse centerline 90. The patent literature is replete with example of such and other components suitable for use in the diapers of the invention, see for example already referred to WO 2017/156200 (Orr et al. P&G) and PCT application CN 2018/110397 filed Oct. 16, 2018 (Erdem et al, P&G), and these will not be discussed in extension herein.

The topsheet 24 is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet 26 is impervious to liquids (e.g., menses and/or urine) and is preferably manufactured from a thin plastic film, although other flexible liquid impervious materials may also be used. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). The backsheet is preferably embossed and/or matte finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

Various absorbent core designs comprising high amount of SAP have been proposed in the past, see for example in U.S. Pat. No. 5,599,335 (Goldman), EP 1,447,066 (Busam), WO 95/11652 (Tanzer), US 2008/0312622A1 (Hundorf), WO 2012/052172 (Van Malderen). In particular the SAP printing technology as disclosed in US 2006/024433 (Blessing), US 2008/0312617 and US 2010/051,166A1 (both to Hundorf et al.) may be used. The invention is however not limited to a particular type of absorbent core. The absorbent core may also comprise one or more glue such as an auxiliary glue applied between the internal surface of one (or both) of the core wrap layers and the absorbent material to reduce leakage of SAP outside the core wrap. A microfibrous adhesive net may also be used in air-felt free cores as described in the above Hundorf references.

The absorbent core is disposed between the backsheet and the topsheet, including the possible presence of other optional layers such as an acquisition layer 54. The function of the acquisition layer is to quickly draw the fluid away from the topsheet to keep the skin as dry. Acquisition layers are typically disposed between the topsheet and the absorbent core. Typical examples of acquisition layers are air-through bonded carded web, with a basis weight ranging typically from 10 gsm to 60 gsm, as is known in the art. Some absorbent articles further have a distribution layer in addition to an acquisition layer, whose function is to distribute the fluid from a region of insult to a larger surface. A typical material for a distribution layer is a layer of loosely bonded cross-linked cellulose fibers as described in the references above (e.g., US 2008/0312,622A1), in order to maximize the speed of absorption of the absorbent core.

Applications

The hydrophilic hotmelt adhesive may be applied onto various substrates including film, nonwoven, cellulose or synthetic fibers, or superabsorbent particles. The hydrophilic hotmelt adhesive may be in particular used to bond a first component which is a nonwoven to a second component of an absorbent article, which may be a second nonwoven, or cellulose fibers, or superabsorbent particles, or a combination thereof. The hydrophilic hotmelt adhesive can also be mixed with cellulose fibers in an airlaid process or as further coating or mixing step to help bonding the fibers and increase integrity of the web. This helps reducing breakage of fibers ("dusting") which can contaminate the converting line when processing the web.

The hydrophilic hotmelt adhesive can in particular facilitates the transfer of a liquid such as urine from one layer to the next layer thanks to its hydrophilicity. The usage of absorbent article may be several hours and cover several liquid insults, so that an hotmelt adhesive having long lasting hydrophilic properties is particularly desirable. The hydrophilic hotmelt adhesives of the invention may be used to attach one or more layer pairs selected from: the topsheet to an acquisition layer, an acquisition layer to a distribution layer, an acquisition or a distribution layer to the absorbent core, a topsheet directly to the absorbent core, or the core wrap to the absorbent material. The attachment between the layers may be over the full interface or partial at the interface. The core wrap, in particular the inner surface of the top side of the core wrap, may be attached to the absorbent layer by the hotmelt adhesive of the invention to facilitate the transfer of liquid from the surface of the core wrap into the absorbent layer. The absorbent layer may be a mixture of cellulose fibers and superabsorbent particles, or superabsorbent particles substantially free of cellulose fibers. The absorbent layer, in particular for absorbent layer consisting of superabsorbent particles without cellulose fibers, may also be immobilized within the core wrap by a hotmelt adhesive according to the invention.

Figure 2:
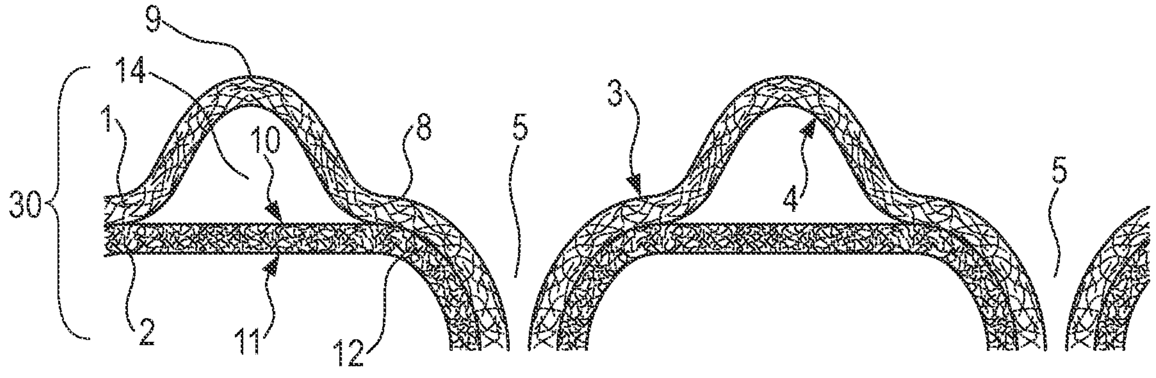
FIG. 2 is a schematic cross-sectional view of a three-dimensional laminate that may be bonded with an adhesive according to the present invention.
Figure 3:
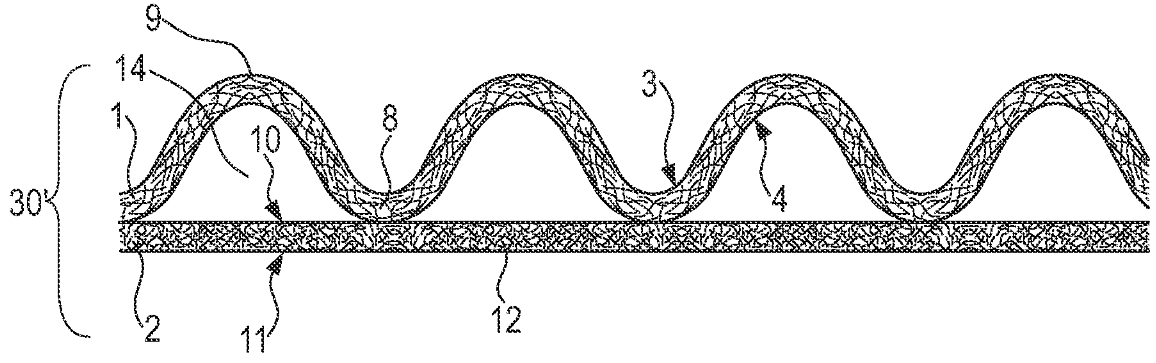
FIG. 3 is a schematic cross-sectional view of an alternative three-dimensional laminate.

The hydrophilic hotmelt adhesive may also be used in three-dimensional laminate, wherein the three-dimensional laminate comprises a first layer and a second layer, the first layer being intermittently bonded to the second layer by the hotmelt adhesive so that the first layer comprises a plurality of protrusions not bonded to the second layer. FIG. 2 and FIG. 3 show two examples of such three-dimensional laminate layer 30 (herein more simply referred to as "the laminate"), which comprises a first layer 1 and a second layer 2. The three-dimensional laminate may be used as topsheet or backsheet in an absorbent article. The first layer may be oriented towards the wearer in the article, and may consists of or comprise of cotton fibers. US 2020/0330291 A1 describes in more details such three-dimensional structures, which may advantageously be hotmelt bonded with the adhesive according to the present invention and used as topsheet in an absorbent article.

The laminate 30 comprises a three-dimensional first layer 1 and a second layer 2. The first layer 1 and the second layer 2 are disposed in a face to face relationship. The first layer 1 comprises a first surface 3 and a second surface 4. The second layer 2 comprises a first surface 10 and a second surface 11. The first surface 10 of the second layer 2 faces the second surface 4 of the first layer 1. The first surface 3 of the first layer 1 and the first surface 10 of the second layer 2 are typically facing outwardly (externally), for example towards the wearer-facing side of the article, while the second surface 4 of the first layer 1 and the second surface 11 of the second layer 2 are typically facing inwardly (internally), when the laminate is incorporated in an absorbent article.

The first layer 1 may be intermittently bonded to the second layer 2 by an hotmelt adhesive according to the present invention. The first layer 1 forms a plurality of protrusions 9 which are unbonded to the second layer 2. The protrusions 9 provide a three-dimensional profile to the first layer 1 and more generally to the laminate as a whole. The first layer 1 and the second layer 2 may be generally contiguous in the horizontal plane, but it is not excluded that the second layer may be wider or longer than the first layer. For example, the second layer may form a secondary topsheet or an acquisition layer that covers a larger area than the first layer. In this example, the first layer may have a smaller area disposed in the central region of the article, relative to the second layer. The protrusions may also be present only in a selected area of the laminate that is smaller than the overall surface of the laminate.

FIG. 2 shows a laminate 30 further comprising apertures 5 extending through the first layer 1 and the second layer 2. Laminates comprising apertures may be in particular used as topsheet 24, or at least to form at least a portion of the topsheet. The apertures 5 in the first layer of the topsheet enable initial and fast fluid flow, especially when the first layer is hydrophobic. Therefore, the first layer of the topsheet, which may be hydrophobic, works in concert with the apertures to reduce wetness on the wearer-facing surface of the topsheet. Such a dual layer topsheet construction is disclosed for example in WO 2015/134359 A1 (Isele at al., P&G) and PCT application CN 2018/110397 filed Oct. 16, 2018 (Erdem et al, P&G). Such apertured laminates may also be disposed on the garment-facing side of the article, especially when attached to a liquid-impermeable polymeric film, to form a liquid impermeable composite backsheet 26.

Laminates 30', such as in FIG. 3, which do not comprise apertures crossing through the laminate may also be disposed on the wearer-facing side, or on the garment facing side of the article. Such a laminate 30' may in particular be used to form at least a portion of, or the whole of, the garment-facing side of the article. A laminate 30' without apertures, as schematically shown in FIG. 2, may also be used as topsheet. In this case, the fibers forming the first and second layers are advantageously not hydrophobically treated.

The adhesive may be applied using multi-line, spray, or slot-coating construction techniques. The adhesive may be in patterned layer of adhesive, or an array of separate lines, spirals, or spots of adhesive. An exemplary attachment means of an open pattern network of filaments comprises several lines of adhesive filaments swirled into a spiral patter. At least one liquid pervious substrate may be bonded to at least one tissue, non-woven, polyolefin or other flexible polymeric film substrate.

In addition, the adhesive of the invention can also be used as a hydrophilic coating to reduce contact angle of the substrates and to enhance hydrophilicity of the substrate surfaces. This can help driving the fluid transferring from a first component to a second component, for example from the topsheet to the acquisition layer, and/or the acquisition/distribution layer to the absorbent core, and/or from the core wrap to the absorbent material within the absorbent core.

Examples

A hotmelt adhesive according to the invention was compounded by blending a metallocene-catalyzed propylene-ethylene copolymer (Licocene PP 2502) with 5% by weight of a hydrophilic hotmelt additive (Techmer PPM 15560). The contact angle Fresh and Aged (15 days at 60° C.) was measured and compared to the pure copolymer. The results were as indicated in table 3.

TABLE 3

| | Copolymer alone | Copolymer + Melt Additive |
|---|---|---|
| Contact Angle Fresh | 92.7 | 22.6 |
| Contact Angle Aged | 85.6 | 20 |

This hotmelt adhesive of the invention was used to make a topsheet-acquisition layer laminate comprising a 12 gsm hydrophilic spunbond topsheet and a 40 gsm air through bonded acquisition layer comprising stable PET and CoPET/PET fibers. The hotmelt adhesive was sprayed at different basis weight. As comparison, a comparative topsheet-acquisition layer laminate was also formed using the copolymer alone.

The laminates using the hotmelt adhesive according to the invention and the comparative laminate were then integrated in Size 4 Pampers Thin & Dry diapers (marketed in China by P&G). The topsheet and acquisition layer of these commercial diapers were replaced by these exemplary laminates.

The run-off performance of these exemplary absorbent articles was tested for consecutive 4 gushes of 75 ml saline water. Results are given in Table 4.

TABLE 4

| | Run off [g] | | | |
|---|---|---|---|---|
| TS/AQL Adhesive – spray application | 1 × 75 ml n = 8 | 2 × 75 ml n = 8 | 3 × 75 ml n = 8 | 4 × 75 ml n = 8 |
| 4 gsm Comparative | 0.2 | 1.1 | 42.3 | 50.8 |
| 4 gsm Inventive | 0.2 | 1.0 | 22.9 | 42.3 |
| 6 gsm Inventive | 0.3 | 0.2 | 6.4 | 17.5 |

Rewet and light touch dryness were also measured using C-GAM, Curved Global Acquisition Method, for 4 consecutive gushes of 75 ml saline water (0.3 psi loading). Results are given in Table 5.

TABLE 5

| TS/AQL Adhesive | Light Touch Dryness [g] 4 × 75 ml n = 8 | Rewet [g] 4 × 75 ml n = 8 | Acq Time 1 × 75 ml n = 16 | Acq Time 2 × 75 ml n = 16 | Acq Time 3 × 75 ml n = 16 | Acq Time 4 × 75 ml n = 16 |
|---|---|---|---|---|---|---|
| 4 gsm | 0.029 | 0.053 | 41 | 54 | 79 | 119 |
| Comparative | (0.004) | (0.003) | (3) | (6) | (8) | (9) |
| 4 gsm | 0.033 | 0.061 | 39 | 53 | 72 | 116 |
| Inventive | (0.005) | (0.004) | (3) | (7) | (6) | (14) |
| 6 gsm | 0.041 | 0.065 | 41 | 53 | 75 | 126 |
| Inventive | (0.014) | (0.004) | (2) | (5) | (7) | (15) |

The data shows that usage of the hydrophilic hotmelt adhesive improves the run-off performance significantly without hurting rewet and light touch dryness performance.

Test Methods

Peak Molecular Weight (Mp) Measurement Method

The peak molecular weight is determined using a gel permeation chromatography (GPC) method. GPC is a well-known method wherein polymers are separated according to molecular size, the largest molecule eluting first. The peak molecular weights referred to herein can be determined with gel permeation chromatography (GPC) using polystyrene calibration standards, such as is done according to ASTM D5296. The molecular weight of any polymer or unknown polymer measured using GPC so calibrated is the styrene equivalent molecular weight, which herein is defined as the "peak molecular weight." Suitable solvents and temperatures are employed with GPC in order to achieve adequate molecular weight separation and resolution.

Enthalpy of Fusion Test Method

The Enthalpy of Fusion Parameter of a hotmelt adhesive composition is determined using the Enthalpy of Fusion Test Method, which consists of performing ASTM D3418-15 with the following additional guidance. Specimen(s) are preferably extracted from molded or pelleted raw material adhesive composition. If raw material is not available, specimen(s) of adhesive are extracted from bonds of interest in an absorbent article using techniques known to those of skill in the art. Dry nitrogen is used as the purge gas in the differential scanning calorimeter (DSC). The rate of increase of temperature in the DSC is 10° C./min, and the rate of decrease of temperature in the DSC is 1° C./min. The mass-normalized enthalpy of fusion is calculated as specified in section 11.4 based on the curve corresponding to decreasing temperature (at 1° C./min) and is reported as the "Enthalpy of Fusion" in units of joules per gram (J/g) to the nearest 0.1 J/g.

Viscosity Test Method

The Viscosity Parameter of a hotmelt adhesive composition is determined using the Viscosity Parameter Test Method, which consists of performing ASTM D3236-15 with the following additional guidance. A Brookfield RVT viscometer with spindle SC 4-27 (Brookfield Engineering, Middleboro, MA, USA), or equivalent, is used. The sample temperature is maintained at 170.0±1.0° C., unless otherwise specified, throughout the measurement. The sample is preheated for 10 minutes and stirred with the measurement spindle for 30 min. The spindle is rotated at 20 rpm throughout the measurement. The resulting apparent viscosity, as described in section 10, is reported as the "viscosity" in units of millipascal-seconds to the nearest 100 mPa·s.

Oscillatory Rheometry Test Method

The Oscillatory Rheometry Test Method is used to measure the Storage Modulus G' and the Loss Factor of a polymer composition. A controlled-strain rotational rheometer (such as Discovery HR-3, TA Instruments, New Castle, DE, USA, or equivalent) capable of sample temperature control (using a Peltier cooler and resistance heater combination) with a precision equal to or exceeding 0.5° C. over at least the range of −10° C. to 150° C. The rheometer is operated in a parallel plate configuration with 20-mm stainless steel parallel-plate tooling.

A parallel plate gap of 1000 μm is initially used in the method. To compensate for thermal expansion of the tooling, the gap is set to 1000 μm, and a mapping of actual plate gap (as measured using a suitable standard test fluid) a function of temperature over the range −10° C. to 150° C. is performed. This mapping is then used throughout the determination of the Storage Modulus Parameter and the Loss Factor Parameter.

The rheometer is heated to 150° C., the polymer composition is introduced in the rheometer, the gap is set to 1050 μm, excess protruding sample is trimmed, and the gap is then set to 1000 μm. (The axial force control of the rheometer is set to 0 N and be maintained within ±0.1 N of force during the experiment, thereby thermal expansion/contraction of the sample itself is compensated by adjusting the gap in order to avoid overfilling or underfilling in addition to the abovementioned compensation of the tooling.) The rheometer is then allowed to cool to 130° C., at which point the measurement commences with temperature ramped from 130° C. to −10° C. at a constant rate of cooling of 2° C./min. The applied strain amplitude is 0.1%, and the frequency of oscillation is 1 Hz (that is, one cycle per second). The resulting oscillatory stress is recorded.

After this step, the sample temperature is set to 23° C. (temperature is ramped to this setpoint at a rate of 10° C./min), and the sample is allowed to rest for 4.0 hours at 23° C. At the end of this period, the temperature is set to −10° C. (temperature is ramped to this setpoint at a rate of 10° C./min), the sample is equilibrated for 300 seconds at −10° C., and a second oscillatory rheology measurement is conducted (0.1% strain, frequency of oscillation of 1 Hz) while temperature is ramped upward to 130° C. at a constant rate of increase of 2° C./min.

From the first decreasing temperature sweep, the storage modulus G' is calculated and recorded at 37° C., and these values are reported in Pascals (Pa) to the nearest 1 Pa as the "Storage Modulus at 100° C.". From the first, decreasing temperature sweep, the loss factor (also known as tan delta) is calculated recorded at 100° C., and this dimensionless value is reported to the nearest hundredth as the "Loss Factor at 100° C.". The storage modulus G' can also be calculated and recorded at different temperatures, for example 60° C.

Contact Angle Method

The Contact Angle Method is used to measure the contact angle of deionized water on a thin film of hotmelt adhesive after 24 hours ("Fresh Film Contact Angle) and accelerated ageing ("Aged Film Contact Angle). Contact angles of deionized water (resistivity 18.2 MΩ or greater at 25° C.) on sample adhesive substrate are determined using the sessile-drop approach generally described in ASTM D7490-13 using a goniometer and appropriate image acquisition system. The goniometer stage is leveled, and the image acquisition system is configured so as to capture toward the center of the stage, along an axis that is in the plane of the stage. The image acquisition system is further configured such that a droplet delivered to the center of the stage is in focus. Contact-angle analysis is carried out under a laboratory environment of 23±2° C. and 40±10% relative humidity.

A continuous adhesive film (at least 50 micrometer thick) is coated on a smooth substrate (e.g. silicone-coated paper) by a hotmelt coater at 170° C. (adapt temperature if needed). The film is then cooled down to ambient lab conditions (21-23° C., 40%-60% RH). The contact angle testing is conducted on the adhesive surface 24 hour after the adhesive coating making.

Five specimen locations from one or more like regions of a sample adhesive are analyzed. Sufficiently many like sample adhesive regions required to provide five specimens 1 cm×1 cm in dimension are selected. The five specimens are excised from the sample adhesive regions. Each specimen is analyzed by first placing it on the leveled goniometer stage. A flat-tipped, 14-gauge needle (outer diameter 2.11 mm) is then used to deliver a 25.0±0.05 μL droplet of deionized water on the center of the specimen. An image of the droplet is captured 5.0 seconds after delivery. Tangent lines are drawn at both horizontal extrema of the imaged droplet, and the angle containing the droplet-substrate interface between each tangent line and the horizontal substrate is measured. The arithmetic mean of these two angles is the contact angle for that specimen and is recorded to the nearest 0.1°. The contact angles for the five specimens are determined in this way. The arithmetic mean of the five specimen contact angles is calculated and recorded as the Fresh Film Contact Angle.

The Aged Film Contact Angle is obtained in similar manner with the difference is that the adhesive film is aged at ambient pressure and at 60±3° C. for 16 days. Subsequently, the adhesive film is kept at 23±2° C. and 40±10% relative humidity for 24 hours immediately prior to contact-angle analysis as indicated above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hydrophilic hotmelt adhesive comprising by weight of the hotmelt adhesive:

from about 30% to about 99% of a metallocene-catalyzed polyolefin, wherein the metallocene-catalyzed polyolefin has a peak molecular weight in the range of from about 10,000 g/mol to about 130,000 g/mol, wherein the peak molecular weight is measured according to the Peak Molecular Weight (Mp) Measurement Method, from about 0.1% to about 10% of a hydrophilic melt additive, wherein the hydrophilic melt additive comprises a first wetting agent and a second wetting agent, and wherein the second wetting agent comprises a water-soluble, nonionic, nonhydrolyzable polyoxyalkylene-modified organosilicone polymer, and from about 0% to about 40% of a tackifier.

2. The hydrophilic hotmelt adhesive according to claim 1, wherein the metallocene-catalyzed polyolefin is propylene-based.

3. The hydrophilic hotmelt adhesive according to claim 1, wherein the hotmelt adhesive has a viscosity at 170° C. in the range of from about 100 mPa·s to about 10,000 mPa·s, as measured by Viscosity Test Method.

4. The hydrophilic hotmelt adhesive according to claim 1, wherein the first wetting agent is a water insoluble nonionic alkoxylated alkyl phenol.

5. The hydrophilic hotmelt adhesive according to claim 1, wherein the hydrophilic melt additive comprises an ethoxylated alcohol.

6. The hydrophilic hotmelt adhesive according to claim 5, wherein the ethoxylated alcohol has the formula:

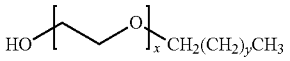

with x ranging from 2 to 100 and y ranging from 12 to 24.

7. The hydrophilic hotmelt adhesive according to claim 1, wherein the hotmelt adhesive exhibits a Fresh Film Contact Angle and an Aged film Contact Angle with distilled water of less than 70 about degrees, as measured by the Contact Angle Method.

8. The hydrophilic hotmelt adhesive according to claim 1, wherein the hotmelt adhesive has a storage modulus (G') higher than about 300,000 Pa at 37° C., wherein the storage modulus is measured with the Oscillatory Rheometry Test Method.

9. An absorbent article comprising a bond formed by the hydrophilic hotmelt adhesive according to claim 1, wherein the article comprises a topsheet, an absorbent core, a backsheet, and optionally an acquisition layer, wherein the absorbent core optionally comprises an absorbent material and a core wrap, wherein the bond formed by the hydrophilic hotmelt adhesive is between two layers selected from:

the topsheet and the optional acquisition layer; or the optional acquisition layer and the absorbent core; or the topsheet and the absorbent core; or the core wrap and the absorbent material.

10. An absorbent article comprising a bond formed by the hydrophilic hotmelt adhesive according to claim 1, wherein the article comprises an absorbent core, the absorbent core comprising an absorbent material layer sandwiched between the top side and the bottom side of a core wrap, the top side being closer to the topsheet than the bottom side, and wherein the hydrophilic hotmelt adhesive is disposed between the top side and the absorbent material layer, and the hydrophilic hotmelt adhesive at least partially immobilizes the absorbent material within the core wrap.

11. An absorbent article comprising a bond formed by the hydrophilic hotmelt adhesive according to claim 1, the article comprising a three-dimensional laminate comprising a first layer and a second layer wherein the first layer is intermittently bonded to the second layer by the hotmelt adhesive so that the first layer comprises a plurality of protrusions not bonded to the second layer, wherein the three-dimensional laminate is a topsheet and the first layer comprises cotton fibers.

12. An absorbent article comprising a bond formed by the hydrophilic hotmelt adhesive according to claim 1, wherein the bond is between a first nonwoven and another component of the article, and wherein the first nonwoven is bonded by the hydrophilic hotmelt adhesive to at least one selected from a second nonwoven, cellulose fibers, or superabsorbent particles.

13. A substrate comprising a coating, wherein the coating is a hotmelt adhesive according to claim 1.

14. The hydrophilic hotmelt adhesive according to claim 1, wherein the metallocene-catalyzed polyolefin has an enthalpy of fusion of from 5 J/g to 45 J/g.

15. The hydrophilic hotmelt adhesive according to claim 1, wherein the hydrophilic hotmelt adhesive is substantially free of tackifier.

16. The hydrophilic hotmelt adhesive according to claim 1, wherein the metallocene-catalyzed polyolefin has a peak molecular weight in the range of from about 10,000 g/mol to about 70,000 g/mol, wherein the peak molecular weight is measured according to the Peak Molecular Weight (Mp) Measurement Method.

17. The hydrophilic hotmelt adhesive according to claim 1, wherein the hydrophilic hotmelt adhesive is permanently hydrophilic.

18. The hydrophilic hotmelt adhesive according to claim 1, wherein the hydrophilic hotmelt adhesive comprises a blend of two or more metallocene-catalyzed polyolefins.

19. An absorbent article comprising a bond formed by a hydrophilic hotmelt adhesive, wherein the article comprises a topsheet, an absorbent core, a backsheet, and optionally an acquisition layer, wherein the absorbent core optionally comprises an absorbent material and a core wrap, wherein the bond formed by the hydrophilic hotmelt adhesive is between two layers selected from:

the topsheet and the optional acquisition layer; or the optional acquisition layer and the absorbent core; or the topsheet and the absorbent core; or the core wrap and the absorbent material;

wherein the hotmelt adhesive comprises, by weight:

from about 30% to about 99% of a metallocene-catalyzed polyolefin, and from about 0.1% to about 10% of a hydrophilic melt additive, and from about 0% to about 40% of a tackifier, wherein the metallocene-catalyzed polyolefin has a peak molecular weight in the range of from about 10,000 g/mol to about 70,000 g/mol, wherein the peak molecular weight is measured according to the Peak Molecular Weight (Mp) Measurement Method, and wherein the hydrophilic melt additive comprises a first wetting agent and a second wetting agent, and wherein the second wetting agent comprises a water-soluble, nonionic, nonhydrolyzable polyoxyalkylene-modified organosilicone polymer;

and wherein the hotmelt adhesive comprises a plasticizer, wherein the plasticizer comprises up to about 20% of the hotmelt adhesive.

* * * * *